United States Patent [19]
Skakoon

[11] Patent Number: 5,232,193
[45] Date of Patent: Aug. 3, 1993

[54] CLAMP FOR INTRAVENOUS TUBING
[75] Inventor: James G. Skakoon, Melrose, Mass.
[73] Assignee: Baxter International Inc., Deerfield, Ill.
[21] Appl. No.: 628,930
[22] Filed: Dec. 12, 1990

Related U.S. Application Data
[63] Continuation of Ser. No. 409,801, Sep. 20, 1989, abandoned.

[51] Int. Cl.⁵ ............................................. F16K 7/02
[52] U.S. Cl. .............................................. 251/4; 24/130
[58] Field of Search ................. 251/4, 7; 24/115 H, 24/115 M, 130, 490, 492

[56] References Cited

U.S. PATENT DOCUMENTS

| | | | |
|---|---|---|---|
| 2,889,848 | 6/1959 | Redmer | 24/130 |
| 2,902,248 | 9/1959 | Barton et al. | 137/613 X |
| 3,910,280 | 10/1975 | Talonn | 24/130 X |
| 4,051,578 | 10/1977 | Manschott et al. | 251/4 |
| 4,063,706 | 12/1977 | Osborne, Sr. | 251/4 |
| 4,355,444 | 10/1982 | Haney | 24/130 X |
| 4,434,963 | 3/1984 | Russell | 251/7 |

FOREIGN PATENT DOCUMENTS

| | | | |
|---|---|---|---|
| 36527 | 11/1885 | Fed. Rep. of Germany | 251/4 |
| 1306369 | 9/1962 | France | 251/4 |

Primary Examiner—John C. Fox
Attorney, Agent, or Firm—Kane, Dalsimer, Sullivan, Kurucz, Levy, Eisele and Richard

[57] ABSTRACT

The present invention is for a clamp for flexible tubing for an infusion or administrative set. The clamp has openings in which the tubing is inserted in a serpentine fashion to form a loop. The friction between the tube and surfaces of the clamp caused by this serpentine configuration allows the clamp to be maintained at any point along the tubing even while it is in the full flow position.

8 Claims, 3 Drawing Sheets

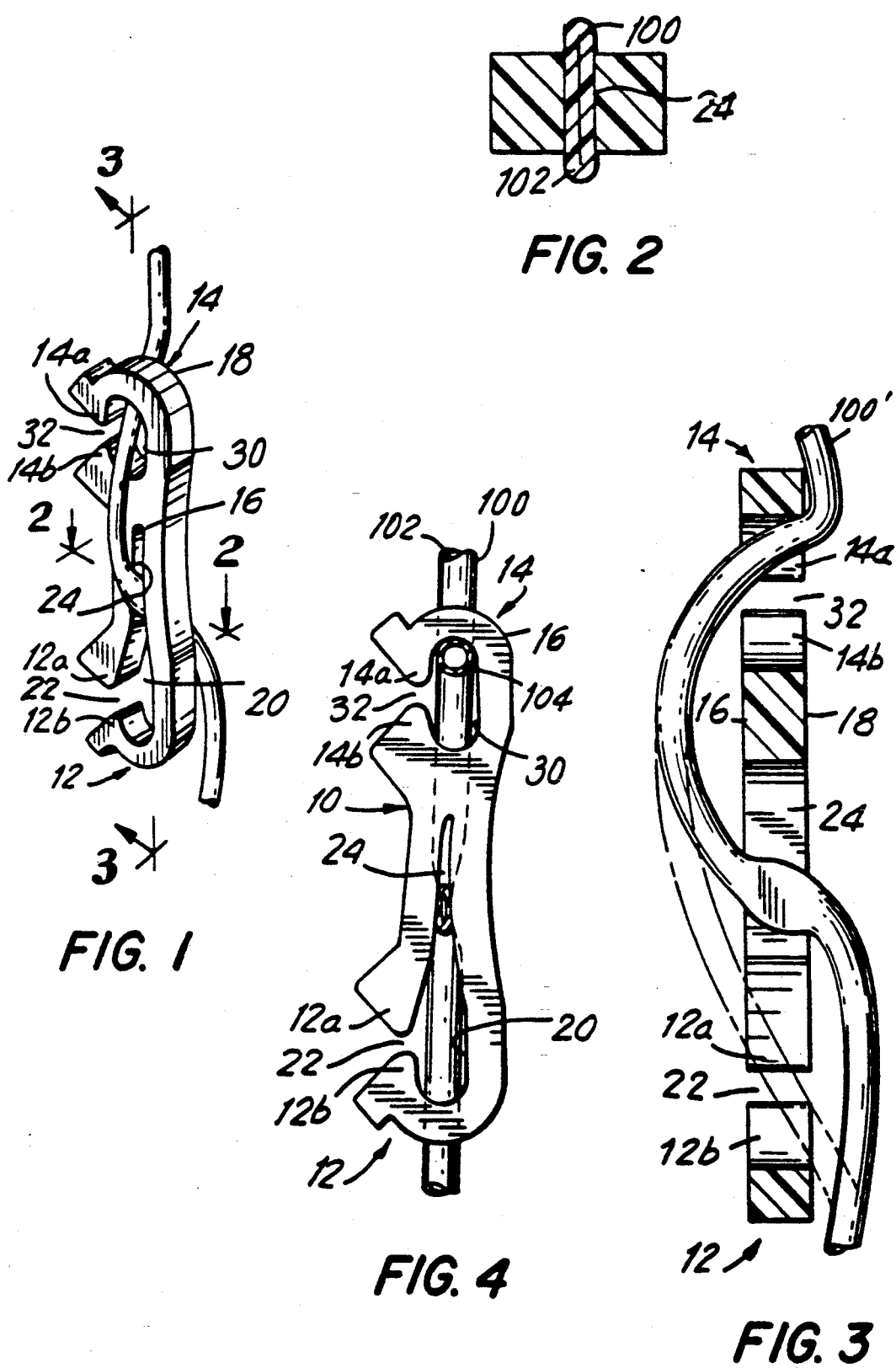

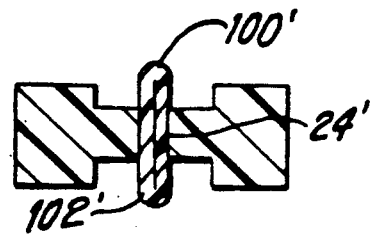
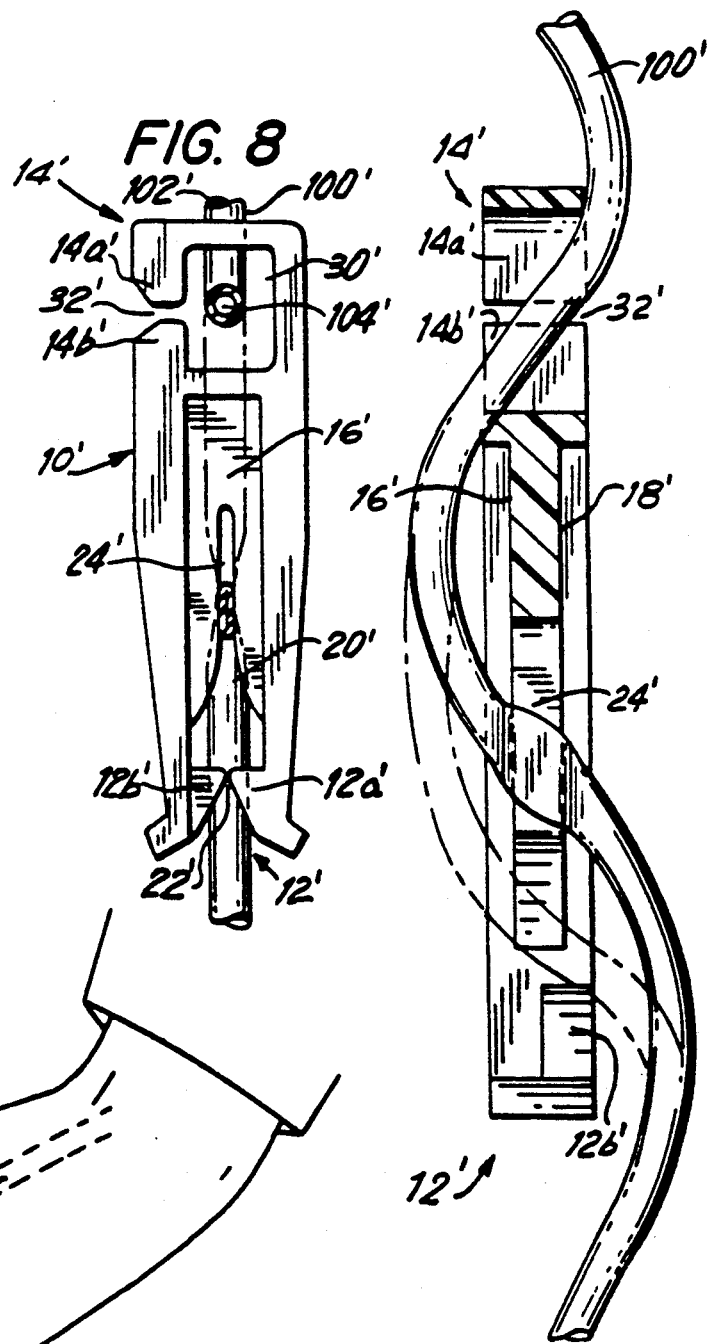
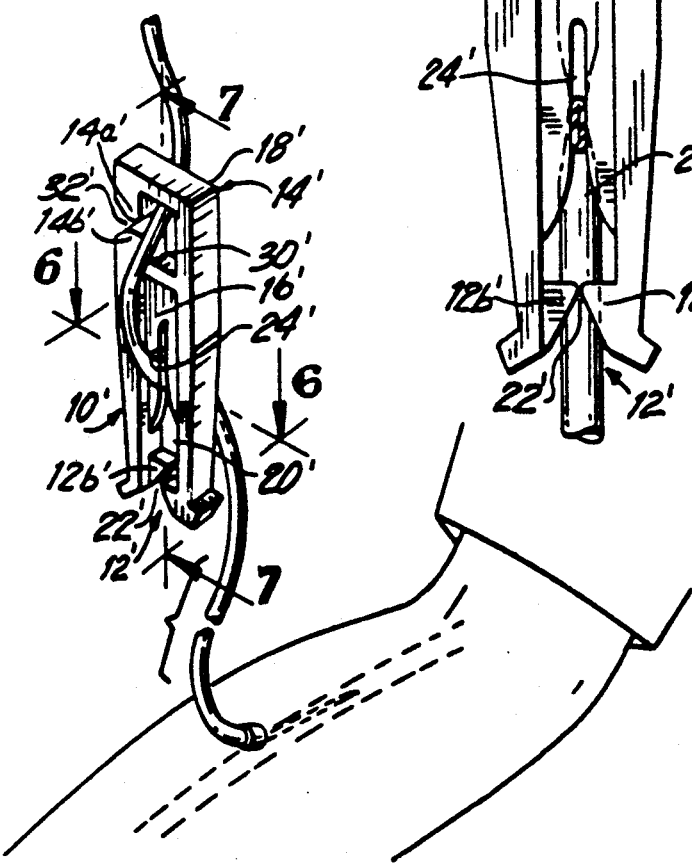

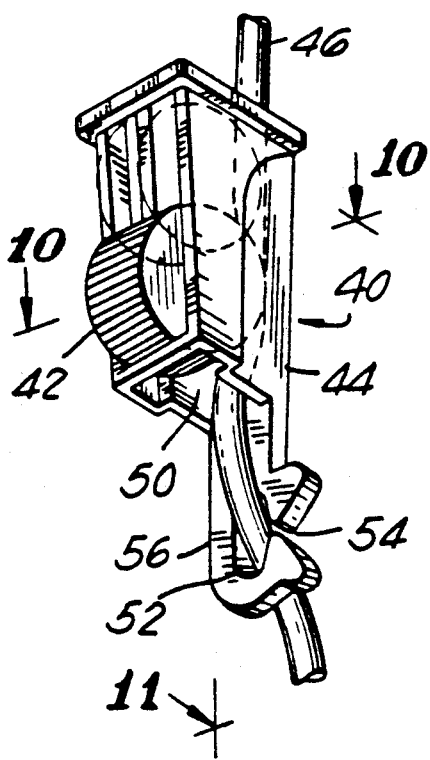
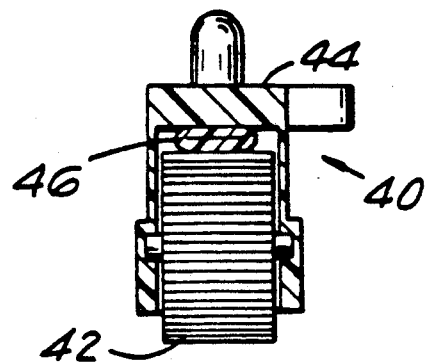
FIG. 10
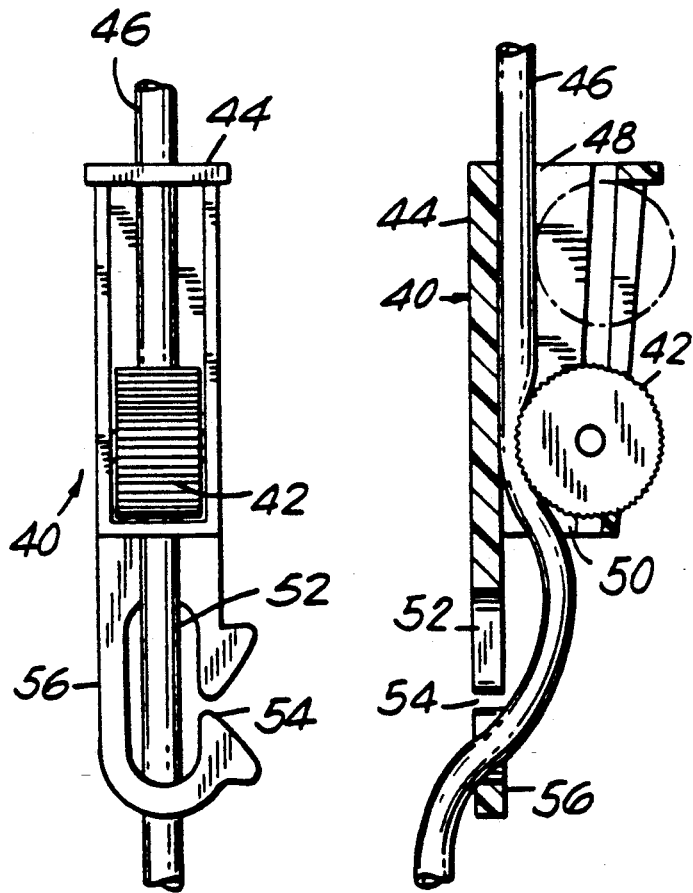
FIG. 9
FIG. 12
FIG. 11

CLAMP FOR INTRAVENOUS TUBING

This is a divisional continuation-in-part of copending application(s) Ser. No. 07/409,801 filed on Sep. 20, 1989 now abandoned.

TECHNICAL FIELD OF THE INVENTION

The present invention relates to tubing clamps and more particularly to slide clamps for medical and intravenous tubing.

BACKGROUND OF THE INVENTION

Slide clamps are used frequently in hospitals to control fluid flow in compressible medical tubing such as, for example, flexible polyvinyl chloride tubing commonly employed in infusion pump sets and parenteral administration sets to deliver drugs, medicament, blood, dextrose solution or other medical fluids to a patient's venous system.

Slide clamps of the foregoing type have been used to adjust fluid flow at different flow rates between full flow and no flow, but they are principally employed as on/off clamps, i.e., to totally occlude the tubing lumen to shut off fluid flow entirely, or to allow for unrestricted fluid flow, without occluding the tubing lumen.

A principal disadvantage inherent with slide clamps used with infusion pumps or parenteral administration sets is that it is difficult to position the clamp and have it remain at a selected point on the tubing length when in the full-flow, or on, position. More often than not, the clamp will slide down the tubing to another location and because of its relatively small size it is difficult to locate immediately. Thus, when a nurse or other operator desires to utilize the clamp to occlude the tubing lumen, precious time must be taken to search for the slide clamp. This is especially so when the infusion pump or administration set, as is often the case, includes many other elements, such as roller clamps, needles, filter housings, check valves, drip chambers and the like.

The infusion pump or administration set is usually disposed substantially vertically, between an infusion pump or a solution container at its upper end and a patient's arm or other venous access site at the lower end. Thus, as the infusion pump or administration set is set up between the solution source and the patient, a slide clamp on the tubing is jostled so that it falls until it rests upon one of the other elements in the set.

The search for the slide clamp is time consuming and bothersome. Once found, the operator will move the slide clamp along the length of tubing to an elevation which does not interfere with any other set element and which is also convenient for use by the operator. Once this is done, the operator will close the slide clamp. However, the slide clamp will usually be reemployed by sliding it along its slot from the lumen occluding "off" mode back to the "on" mode. When the slide clamp is readjusted to the "on" mode, it will once again slide down the tubing, making necessary a still subsequent search if it is to be used again.

Attempts have been made to solve this problem, as shown in U.S. Pat. No. 2,889,848 to Redmer. Redmer employs a two piece structure including a slide-type clamp, in conjunction with a clamp body section or block. The Redmer clamp is designed for being maintained at a given elevation while in the on position by carefully dimensioning the block bore to the tubing diameter. Thus, the Redmer clamp may be used with essentially only one tubing size. Also, the Redmer clamp is relatively expensive to manufacture. One of the key advantages of slide clamps is that they are inexpensive. If the cost of a slide clamp is too great, other devices, such as roller clamps, can easily be used.

In U.S. Pat. No. 4,434,963 issued to Russell, a slide clamp is disclosed which purportedly addressed the above disadvantages. This slide clamp includes a stabilizer which together with cocking or angular tilting of the clamp on the tubing permits the clamp to remain at the selected elevation. The Russell clamp remains problematic because in actual practice the clamp does slide down the tubing during use and abuse by the attending staff, particularly when the clamp is not tilted.

Another disadvantage of many known slide clamps is that they must be installed during manufacture as opposed to being added by a nurse or other operator during use. Further, the clamp cannot be removed if desired. The clamp shown in Redmer and Russell may be added or removed at the time of use but the former necessitates keeping track of two separated pieces and suffers from the other disadvantages discussed above. Nevertheless, Redmer and Russell have proven to be ineffective attempts at maintaining slide clamps at the desired elevation on tubing.

SUMMARY OF THE INVENTION

The slide clamps of the present invention solve all of the above problems and are of simple construction and inexpensive to manufacture. A principal object of the invention is to provide a slide clamp that may be selectively positioned and maintained at any point along a length of flexible tubing while in the open, or "on" mode. While maintaining their position at any elevation, the slide clamps may be easily moved along the length of tubing without overcoming a strong interference fit between the slide clamp and tubing.

The slide clamps of the present invention include an elongated member with first and second ends, the first end with an opening having a bifurcation which defines a tapered slot for receiving a tube and a second end having a channel communicating with an opening that also receives the tube in a serpentine fashion with respect to the tapered slot, thus causing the tube to bend longitudinally to form a loop. This distortion causing friction between the clamp and the tube sufficient to prevent undesired movement of the clamp, and, permitting it to remain substantially in one place with respect to the tubing. The tapered slot serves to severely restrict the tubing lumen, thereby preventing or severely limiting fluid flow.

Another object of the invention is to provide a slide clamp with two receiving portions adjacent to each slot to enable installation or removal of the clamp onto or from the tubing subsequent to the manufacture of the administrative set.

A further object according to the invention is to provide a clamp that may be used with a broad range of tubing sizes and wall thicknesses.

Still another object is to adapt the attributes of the invention to a roller-type clamp.

BRIEF DESCRIPTION OF THE DRAWINGS

FIG. 1 is a fragmentary perspective view of the preferred embodiment of clamp of the invention shown associated with tubing and being in a flow restrictive position;

FIG. 2 is a cross-sectional view taken along the line 2—2 of FIG. 1 of the slide clamp, showing it in a restrictive position;

FIG. 3 is a side view in section taken along the line 3—3 of FIG. 1 of the slide clamp, illustrating a restrictive flow position and the full flow position in phantom;

FIG. 4 is a front elevational view of the slide clamp showing the restrictive position;

FIG. 5 is a fragmentary perspective view of another embodiment of clamp of this invention shown associated with tubing leading into a patient's arm and in a flow restrictive position;

FIG. 6 is a cross-sectional view thereof taken along the line 6—6 of FIG. 5;

FIG. 7 is a side view thereof in section taken along the line 7—7 of FIG. 5 with the full flow position shown in phantom;

FIG. 8 is an elevational view thereof;

FIG. 9 is a fragmentary perspective view of a roller clamp incorporating the teachings of this invention in a flow restricted position;

FIG. 10 is a sectional view taken along the line 10—10 of FIG. 9;

FIG. 11 is a longitudinal sectional view taken along the line 11—11 of FIG. 9 with the full flow position of the roller shown in phantom; and FIG. 12 is an elevational view thereof.

DETAILED DESCRIPTION OF THE PREFERRED EMBODIMENT

The preferred embodiment of the invention is embodied in a slide clamp 10 which may be selectively positioned and maintained at any point or elevation along a length of flexible tubing 100 while the clamp is in the full-flow or on mode. The clamp 10 is comprised of an elongated member with a first end 12 with first opening 20 and a second end 14 with a second opening 30 with each having a receiving channel portion 22 and 32, respectively. First opening 20 contains tubing restricting tapered slots 24. Channels 22 and 32 separate ends 12 and 14 respectively into leg halves 12a and 12b for the first end and 14a and 14b for the second end.

Leg halves 12a,12b and 14a,14b extend inwardly and are capable of flexure toward and away from each other, thus aiding mounting the clamp 10 about the tubing 100 through channels 22 and 32 and also facilitating the selective positioning of the clamp 10 at any selected elevation on the tubing 100.

In the preferred embodiment legs 12a,12b,14a and 14b are rounded contact areas so as to minimize damage to the tubing.

Clamp 10 may be mounted about the tubing 100 by either threading the tubing through the slots 20 and 30 or else by sliding the tubing through channels 22 and 32 in such a fashion so the tubing is longitudinally bent and forms a loop so that part of tubing 100 is on first side 16 of the elongated member and part is on second side 18 of the elongated member. The loop assures the maintenance of the selected elevation of the clamp 10 along tubing 100.

The longitudinally bent or serpentine tubing configuration through the elongated member results in friction between clamp 10 and tubing 100. Such friction causes forces adequate to withstand the weight of clamp 10.

Because the slide clamp's physical dimensions are correct with respect to the tubing, its presence on the tubing in the full-flow position does not impinge on the tubing wall 102 in any fashion that might substantially restrict the tubing lumen 104, i.e. in the on or full-flow position the tubing cross-section remains substantially unchanged. Fluid may flow freely through the lumen 104 at the open position of the slide clamp 10. As a result of the loop in the tubing 100 and the frictional forces resulting from the engagement of the tubing with surfaces of the clamp, the clamp will remain at the selected elevation and will not move unintentionally along the tubing.

The slide clamp 10 is moved from the free-flow position to a restricted flow position as shown in FIG. 3 in the normal manner, i.e. the slide clamp 10 is manually moved against the tubing so that the tubing enters the tapered slot 24 to a position that will restrict the flow of fluid to the desired rate.

To change the elevation of slide clamp 10, the tubing is placed in openings 20 and 30. The clamp is then moved manually. Such manual movement easily overcomes the aforementioned friction forces occurring due to the serpentine tubing configuration.

In the alternate embodiment of the invention shown in FIGS. 5–8, like parts are similarly numbered with an accompanying prime. Clamp 10' may be moved along the length of tubing 100' by disposing the tubing in openings 20' and 30' and then manually sliding it to the desired location. As a result of the formed loop and the frictional engagement of the tubing 100' with surfaces of the clamp 10', the clamp will remain at this elevation even in the fully open position.

Reference is now made to FIGS. 9–12 wherein a roller clamp 40 which includes the usual roller 42 shiftable in housing 44 between a first position, shown in phantom in FIGS. 9 and 11, at which tubing 46 is fully distended for unimpeded fluid flow and a second position, at which it compresses the tubing to stop the flow. In this regard, the tubing 46 passes through opening 48 and out through opening 50 both in housing 44.

As with the previous embodiments, a loop is formed in the tubing 46 for inducing frictional engagement of the tubing 46 with the housing 44. Towards that end, tubing 46 enters opening 52 after insertion through channel 54 in extension 56 of the housing 44. Thus, when the roller 42 is in its elevated position at which full fluid flow through the tubing 46 occurs, the roller clamp 40 will not fall or slip down the tubing 46 because of its frictional engagement with surfaces of the housing 44.

Thus, the several aforenoted objects and advantages are most effectively attained. Although several embodiments have been disclosed and described herein, it should be understood that this invention is in no sense limited thereby and its scope is to be determined by that of the appended claims.

What is claimed is:

1. A tubing clamp for variably controlling flow through a medical tube, comprising:
   a planar body having a longitudinal axis defined by a direction of travel of the medical tube;
   a first opening and a second opening formed along said longitudinal axis of said planar body, said first opening including a tapered slot with a major axis coincident with said longitudinal axis, said tapered slot including a narrow portion toward an interior of said body and a wide portion toward an end of said body, said wide portion dimensioned to fully distend a lumen of the medical tube forming an "on" mode, said narrow portion dimensioned to restrict the lumen of the medical tube forming an "off" mode, said tapered slot further including portions of gradually narrowing widths between said wide portion and said narrow portion dimensioned to variably control flow through the lumen of the medical tube;

said second opening being of a rounded shape so as to slidably position the tubing clamp along the medical tube and frictionally engage the medical tube.

2. The clamp of claim 1 wherein channels are provided in the clamp in communication with said first and second openings to facilitate insertion or removal of the tube into or from said first and second openings.

3. The clamp of claim 2, wherein the clamp is a slide clamp and is adapted to be mounted directly on the tube by having the tube put through said channels in a serpentine fashion.

4. The slide clamp of claim 3, wherein said first and second channels are adjacent to said first opening and said second opening to enable installation of the slide clamp onto the tube subsequent to the set-up of an administrative or infusion set.

5. The combination of a medical tube and a tubing clamp for variably controlling flow through the medical tube, the tubing clamp comprising:

a planar body having a longitudinal axis defined by a direction of travel of the medical tube;

a first opening and a second opening formed along said longitudinal axis of said planar body, said first opening including a tapered slot with a major axis coincident with said longitudinal axis, said tapered slot including a narrow portion toward an interior of said body and a wide portion toward an end of said body, said wide portion dimensioned to fully distend a lumen of the medical tube forming an "on" mode, said narrow portion dimensioned to restrict the lumen of the medical tube forming an "off" mode, said tapered slot further including portions of gradually narrowing widths between said wide portion and said narrow portion dimensioned to variably control flow through the lumen of the medical tube;

said second opening being of a rounded shape so as to slidably position the tubing clamp along the medical tube and frictionally engage the medical tube.

6. The combination according to claim 5, wherein channels are provided in the clamp in communication with said first and second openings to facilitate insertion of the tube into said first and second openings.

7. The combination according to claim 6, wherein the clamp is a slide clamp and is adapted to be mounted directly on the tube by having the tube put through said channels in a serpentine fashion.

8. The invention according to claim 7, wherein said first and second channels are adjacent to said first opening and said second opening to enable installation of the slide clamp onto the tube subsequent to the manufacture of an administrative set.

* * * * *